Figure 1:
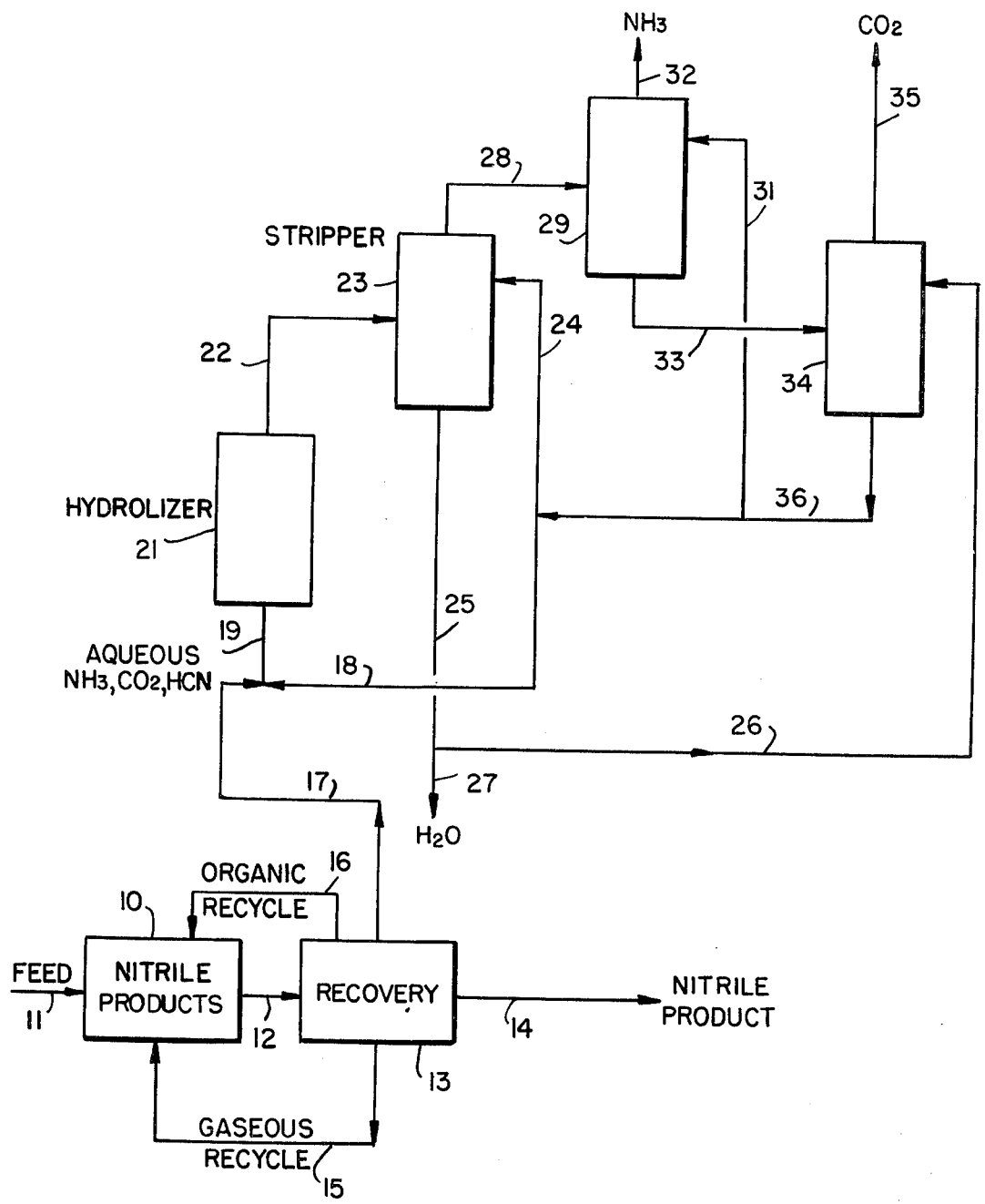

United States Patent [19]

Gelbein et al.

[11] 4,148,865

[45] Apr. 10, 1979

[54] TREATMENT OF CYANIDE BYPRODUCT IN NITRILE PRODUCTION

[75] Inventors: Abraham P. Gelbein, Plainfield; Joon T. Kwon, Freehold Township, Monmouth County, both of N.J.

[73] Assignee: The Lummus Company, Bloomfield, N.J.

[21] Appl. No.: 867,520

[22] Filed: Jan. 6, 1978

[51] Int. Cl.² ............................................. C07C 120/14
[52] U.S. Cl. .................................... 423/358; 423/236; 260/465.3; 260/465.9
[58] Field of Search ............... 423/236, 238, 355, 358; 55/68; 260/465.3, 465.9

[56] References Cited

U.S. PATENT DOCUMENTS

| | | | |
|---|---|---|---|
| 2,459,464 | 1/1949 | Smith | 423/355 |
| 3,386,804 | 6/1968 | Neugebauer et al. | 423/352 |
| 3,878,289 | 4/1975 | Beavon | 55/68 X |
| 4,065,486 | 12/1977 | Thorpe et al. | 260/465.9 X |

FOREIGN PATENT DOCUMENTS 2141294  2/1973  Fed. Rep. of Germany ........... 423/236

*Primary Examiner*—G. O. Peters
*Attorney, Agent, or Firm*—Marn & Jangarathis

[57] ABSTRACT

Hydrogen cyanide, carbon dioxide and ammonia present in a nitrile production effluent are recovered as an aqueous solution containing ammonium carbonate and ammonium cyanide. The cyanide is hydrolyzed to ammonia and carbon monoxide, followed by recovery of carbon monoxide, carbon dioxide and ammonia, all free of cyanide, from the hydrolyzed solution. In this manner, ammonium values are recovered from the cyanide byproduct and recovered streams are free of cyanide.

16 Claims, 2 Drawing Figures

TREATMENT OF CYANIDE BYPRODUCT IN NITRILE PRODUCTION

This invention relates to the production of nitriles and more particularly to a new and improved process for treatment of cyanide byproduct produced in the manufacture of nitriles.

In the production of nitriles by an ammoxidation process, which involves reaction between an organic compound, ammonia and oxygen, (provided directly or by the use of an oxidized catalyst) small amounts of hydrogen cyanide and/or ammonium cyanide are produced as byproduct. Such cyanides are highly toxic substances which cannot be discharged into the atmosphere, and as a result, there is a need for a new and improved process for treating such cyanide byproducts to prevent release thereof into the atmosphere.

An object of the present invention is to provide for treatment of cyanide byproduct generated in the production of nitriles.

Another object of the present invention is to treat cyanide byproduct in a manner to recover ammonium values therefrom.

These and other objects of the present invention should be more readily apparent from reading the following detailed description thereof.

In accordance with the present invention, there is recovered from a nitrile production effluent hydrogen cyanide and at least a portion of the carbon dioxide and ammonia, as an aqueous solution containing ammonium carbonate and ammonium cyanide, with the cyanide being subsequently hydrolyzed to ammonia and carbon monoxide. Ammonia, carbon monoxide and carbon dioxide, all free of cyanide, are then recovered from the hydrolysis product. In this manner, ammonium values can be effectively recovered from the cyanide byproduct. In addition, recovered water, as well as the recovered gas are free of cyanide.

The hydrolysis of cyanide present in an aqueous ammonium carbonate/ammonium cyanide solution is generally effected at a temperature of from about 100° F. to about 400° F., whereby the ammonium cyanide is converted to ammonia and carbon monoxide. The hydrolysis is generally effected at the autogenous pressure of the system; however, higher pressures could be employed. The contacting is effected for a period of time to achieve the desired per pass conversion of cyanide at the hydrolysis temperature. It is not necessary to achieve 100% per pass conversion of cyanide in that 100% total conversion of net cyanide can be achieved by providing for recycle, as hereinafter described.

In accordance with one embodiment of the present invention, an aqueous solution of ammonium carbonate and ammonium cyanide, recovered from a nitrile production effluent, is subjected to hydrolysis conditions to convert hydrogen cyanide to ammonia and carbon monoxide. The hydrolysis product is introduced into a stripping zone to strip volatiles from this solution and thereby provide a liquid product of essentially pure water, which is free of cyanide. The stripped gaseous mixture, containing water vapor, ammonia, carbon monoxide, carbon dioxide and unconverted hydrogen cyanide is then introduced into an ammonia recovery zone to effect recovery of ammonia therefrom. In particular, ammonia is recovered in a stripper-absorber, wherein the gaseous mixture is contacted with an ammonia rich ammonium carbonate solution to provide an ammonia gas stream containing carbon monoxide produced in the hydrolysis, a carbon dioxide rich ammonium carbonate solution, and any unconverted ammonium cyanide. The solution is then introduced into a stripper to strip carbon dioxide therefrom, and provide an ammonia rich ammonium carbonate solution. A portion of the ammonia rich ammonium carbonate solution is recycled to the hydrolysis in order to effect hydrolysis of any remaining unconverted hydrogen cyanide which was present in the feed to the hydrogen cyanide recovery operation. A further portion of the ammonia rich ammonium carbonate solution is recycled to the stripper-absorber for recovering ammonia. The recovered ammonia may be recycled to the nitrile production, with any carbon monoxide present in the ammonia being ultimately purged from the system.

In accordance with another embodiment of the present invention, an aqueous solution of ammonium carbonate and ammonium cyanide, recovered from a nitrile production effluent, is stripped of volatiles to provide a liquid stream of essentially pure water, free of cyanide, and a gaseous mixture of water vapor, ammonia, carbon dioxide and hydrogen cyanide. The gaseous mixture is then introduced into an ammonia recovery zone, which is preferably a stripper-absorber, wherein ammonia, free of cyanide, is recovered from the gaseous mixture by the use of an ammonia rich ammonium carbonate absorption solution. Ammonia is recovered as a gaseous stream from the stripper-absorber and may be recycled to the nitrile production. A liquid stream, which is a carbon dioxide rich ammonium carbonate solution, containing ammonium cyanide, is then subjected to hydrolysis to convert the cyanide in the solution to ammonia and carbon monoxide. The hydrolysis effluent is then introduced into a stripper to strip carbon dioxide and carbon monoxide, free of cyanide, from the solution and provide an ammonia rich ammonium carbonate solution. Ammonia rich ammonium carbonate solution recovered from the stripping of carbon dioxide and carbon monoxide is employed in the stripper absorber for recovering ammonia.

The aqueous solution of ammonium carbonate and ammonium cyanide is recovered from a nitrile production effluent generated in a process for producing aromatic, aliphatic or heterocyclic nitriles. As representative examples of such nitriles, there may be mentioned aromatic nitriles which contain one or more cyano groups, preferably one or two cyano groups, which can be unsubstituted or substituted with other substituent groups; for example, an alkyl group, such as phthalonitrile, terephthalonitrile, isophthalonitrile, tolunitrile, 1-cyanonaphthalene, 2,6-cyanonaphthalene, etc., or a heterocyclic nitrile containing one or more cyano groups, with the heterocyclic nucleus generally being pyridine, such as nicotinonitrile; or an aliphatic nitrile, such as acrylonitrile, methacrylonitrile, etc. Such nitriles are generally produced by the ammoxidation process. The process for producing such nitriles are well known in the art and, accordingly, no details in this respect are needed for a complete understanding of the present invention.

Figure 2:
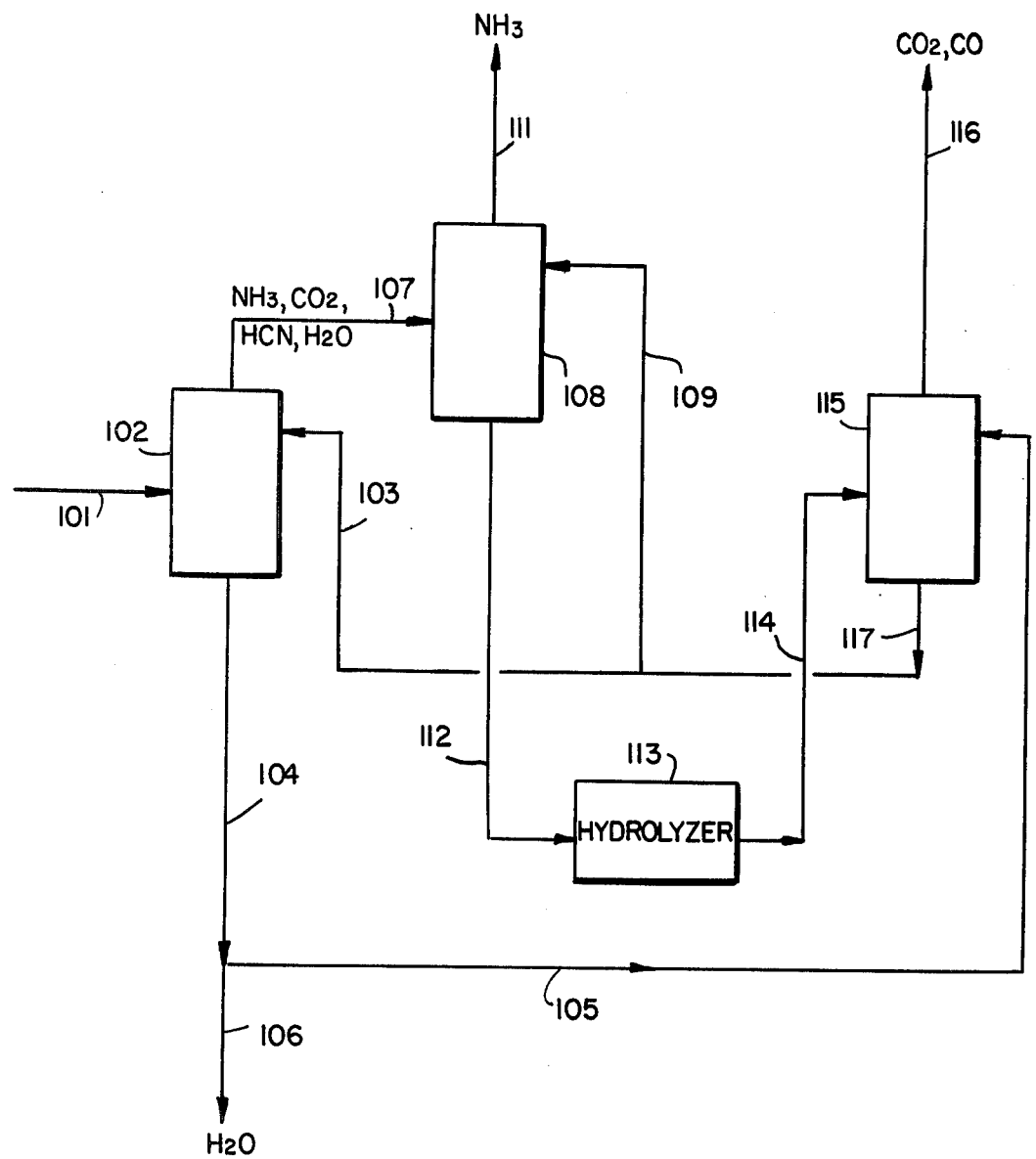

The present invention will be further described with respect to embodiments thereof illustrated in the accompanying drawings wherein:

FIG. 1 is a simplified schematic flow diagram of one embodiment of the present invention; and FIG. 2 is a simplified schematic flow diagram of another embodiment of the present invention.

Referring now to FIG. 1 of the drawings, there is schematically illustrated a nitrile production reaction zone, generally indicated as 10, which is provided with a suitable feed through line 11. The feed in line 11 includes an organic material to be converted to a nitrile, ammonia, and may further include oxygen in the case where oxygen requirements are to be provided by gaseous oxygen. Alternatively, as hereinabove noted, oxygen requirements for the process may be provided by the use of a suitable catalyst, such as, for example, oxidized vanadia on a suitable support.

A nitrile production reaction effluent is withdrawn from reaction zone 10 through line 12, and such effluent generally includes unreacted feed material, nitrile product, organic intermediates, organic byproducts, water vapor, ammonia, carbon dioxide and hydrogen cyanide, and such effluent is introduced into a recovery zone, schematically generally indicated as 13. In the recovery zone, there is recovered nitrile product through line 14, an ammonia containing recycle stream through line 15 and an organic recycle stream through line 16. In the recovery zone 13, there is also recovered an aqueous stream, containing ammonium carbonate and ammonium cyanide, through line 17. The operation of such a recovery zone is known in the art, and forms no part of the present invention. In general, in recovery zone 13, the nitrile production effluent is contacted with a suitable quench liquid to recover a liquid stream containing nitrile product, and a gaseous stream containing organics, as well as water vapor, carbon dioxide, ammonia and hydrogen cyanide. The remaining gaseous stream is then further cooled to separate an organic condensate, an aqueous condensate, which contains ammonium carbonate and ammonium cyanide and a remaining ammonia containing gaseous recycle stream.

The aqueous solution of ammonium carbonate and ammonium cyanide, in line 17, is combined with a recycle stream in line 18, obtained as hereinafter described, and the combined stream in line 19 introduced into a hydrolyzer, schematically generally indicated as 21. In hydrolyzer 21, as hereinabove described, hydrogen cyanide is hydrolyzed to produce ammonia and carbon monoxide. In general, it is not possible to effect complete hydrolysis of the hydrogen cyanide in hydrolyzer 21, and as a result, the hydrolysis effluent still contains ammonium cyanide.

A liquid hydrolysis effluent, containing dissolved ammonium carbonate and a reduced quantity of ammonium cyanide is withdrawn from hydrolyzer 21 through line 22 and introduced into a solution stripper, schematically generally indicated as 23, along with an ammonia rich ammonium carbonate solution in line 24, obtained as hereinafter described. The stripper 23 is operated at conditions to strip all of the volatiles from the aqueous solution and provide essentially pure water, free of cyanide, as a liquid product. In general, the stripper is operated at a temperature of from 150° F. to 250° F. and a pressure of from 1 to 2 atm. It is to be understood, however, that the scope of the invention is not limited to such conditions.

Essentially pure water, free of cyanide, is withdrawn from the stripper 23 through line 25, and a first portion thereof passed through line 26 for use as hereinafter described. The remaining portion of the water is discarded through line 27.

A gaseous overhead stream, containing ammonia, carbon dioxide, carbon monoxide, hydrogen cyanide and water vapor is withdrawn from stripper 23 through line 28 and introduced into an ammonia recovery zone, in the form of a stripper-absorber, schematically generally indicated as 29. The stripper-absorber 29 is operated to recover a gaseous stream of ammonia and carbon monoxide, free of cyanide, and an aqueous liquid stream of a carbon dioxide rich ammonium carbonate solution, containing ammonium cyanide. The stripper 29 is provided with an ammonia rich ammonium carbonate solution through line 31, which is obtained as hereinafter described. In general, the stripper-absorber 29 is operated at a temperature in the order of from about 120° F. to 200° F., and a pressure in the order of from about 1 to about 2 atm.

Gaseous ammonia recovered from the stripper-absorber 29 through line 32 can be recycled to the nitrile production reactor 10, with any contained carbon monoxide being ultimately purged from the system.

A carbon dioxide rich aqueous solution of ammonium carbonate and unconverted ammonium cyanide is withdrawn from stripper-absorber 29 through line 33, and introduced into a stripper, generally schematically indicated as 34, for stripping carbon dioxide from the solution. The ammonium cyanide concentration in the solution is sufficiently low that cyanide is not stripped from the solution. The stripper 34 is also provided with water through line 26 in order to scrub ammonia from the vapor generated in the stripper 34. The stripper 34 is generally operated at a temperature from 200° F. to 400° F., and at a pressure of from 5 to 20 atm. It is to be understood, however, that such conditions are illustrative and the scope of the invention is not to be limited thereby.

Carbon dioxide, free of cyanide, is withdrawn from stripper 34 through line 35, and since such gaseous stream in line 35 is free of cyanide values, such stream may be purged to the atmosphere.

An ammonia rich aqueous ammonium carbonate solution, containing some ammonium cyanide, is recovered from stripper 34 through line 36. A first portion of the stream is employed in line 31 for absorbing carbon dioxide introduced into the stripper absorber through line 28.

A further portion thereof is provided to the solution stripper 23 through line 24. Another portion thereof is passed through line 18 for recycle to the hydrolyzer 21 in order to effect hydrolysis of the residual cyanide, as hereinabove described. By effecting recycle of a portion of the bottoms from the carbon dioxide stripper 34, there is obtained essentially complete hydrolysis of the cyanide values present in the aqueous stream in line 17.

A further embodiment of the present invention is illustrated in FIG. 2 of the drawings. Referring now to FIG. 2, an aqueous solution of ammonium carbonate and ammonium cyanide, in line 101, obtained from a nitrile production effluent, as hereinabove described with reference to the embodiment of FIG. 1, is introduced into a solution stripper 102, along with an ammonia rich ammonium carbonate solution in line 103, obtained as hereinafter described. The stripper 102 is operated at conditions to strip all of the volatiles from the aqueous solution and provide essentially pure water, free of cyanide, as hereinabove described with respect to the solution stripper 23.

Essentially pure water, free of cyanide, is withdrawn from the stripper 102 through line 104, and a first portion thereof passed through line 105 for use as hereinafter described. The remaining portion of the water is discarded through line 106.

A gaseous overhead stream of ammonia, carbon dioxide, hydrogen cyanide and water vapor is withdrawn from stripper 102 through line 107 and introduced into a stripper-absorber 108, which is operated as hereinabove described with respect to stripper-absorber 29. The stripper absorber 108 is provided with an ammonia rich ammonium carbonate solution through line 109.

An ammonia overhead, free of cyanide, is withdrawn from stripper-absorber 108 through line 111 and may be recycled to the nitrile production reactor.

A carbon dioxide rich aqueous solution of ammonium carbonate and ammonium cyanide is withdrawn from stripper-absorber 108 through line 112 and introduced into a hydrolyzer 113, wherein the ammonium cyanide is hydrolyzed to ammonia and carbon monoxide, as hereinabove described.

A hydrolysis effluent is withdrawn from hydrolyzer 113 through line 114 and introduced into a stripper 115 for stripping carbon monoxide and carbon dioxide. The stripper 115 is also provided with water through line 105 for effecting scrubbing of ammonia from the vapor generated in the stripper.

Gaseous carbon monoxide and carbon dioxide, free of cyanide, is withdrawn from stripper 115 through line 116 and may be purged to the atmosphere.

An ammonia rich ammonium carbonate solution is withdrawn from stripper 115 through line 117, and a first portion thereof is passed through line 109 for introduction into the stripper-absorber 108. A further portion thereof is passed through line 103 for introduction into the solution stripper 102.

The present invention will be further described with respect to the following examples; however, the scope of the invention is not to be limited thereby:

EXAMPLE I

This example demonstrates the ability to hydrolyze cyanide in an aqueous solution in accordance with the embodiment of FIG. 1.

The tests were conducted in a continuous vertical hydrolysis reactor made of 316 stainless steel—1" O.D. × 13" height, with a thermowell down the length of the reactor. The liquor was charged upward. The bottom 3-4" section of the reactor served as the preheater. The total liquor holdup volume of the reactor was 135±5cc. The overflow was collected in a cold knockout. The system pressure was maintained at 50-100 psig over the normal vapor pressure during operation. The cyanide concentration was determined by an argentometric titration method. Ammonia and carbon dioxide contents were determined by acidometric titrations. Operating conditions and results are in table I.

TABLE I

| Test No. | 1 | 2 | 3 | 4 |
|---|---|---|---|---|
| Feed Composition (wt%) | | | | |
| $NH_3$ | 17.44 | 18.72 | 18.06 | 18.06 |
| $CO_2$ | 5.93 | 5.94 | 6.02 | 6.02 |
| $NH_4CN$ | 0.128 | 0.107 | 0.120 | 0.120 |
| Hydrolysis Conditions | | | | |
| Temperature (°C.) | 138 | 138 | 152 | 158 |
| Contact Time (min.) | 35 | 45 | 80 | 80 |
| Net Run Time (min.) | 260 | 375 | 185 | 60 |
| Residual $NH_4CN$ (wt%) | 0.035 | 0.034 | 0.023 | 0.018 |
| %Hydrolyzed | 72.7 | 69.2 | 80.8 | 85.0 |

EXAMPLE II

This example demonstrates the ability to hydrolyze cyanide in an aqueous solution in accordance with the embodiment of FIG. 2.

The test was conducted in a batch 155 cc 316 stainless steel reactor. Operating conditions and results are in Table II.

TABLE II

| | | |
|---|---|---|
| Feed Comosition (wt%) | | |
| $NH_3$ | | 15.10 |
| $CO_2$ | | 17.54 |
| HCN | | 0.63 |
| Hydrolysis Conditions | | |
| Hydrolysis Time (mins.) | | 30 |
| Heat-up Time (mins.) | | 12 |
| Reaction Temperature (°C.), | mean | 139 |
| | range | 137-140 |
| Pressure (psia) | | 600 |
| Cooling Time (mins.) | | 22 |
| Liquor Charged (cc) | | 80.0 |
| Residual $NH_4CN$ (wt%) | | 0.014 |
| % $NH_4CN$ Hydrolyzed | | 97.8 |

The present invention is particularly advantageous in that it is possible to remove hydrogen cyanide by-product produced in a nitrile production process, without release of cyanide values into the atmosphere. Moreover, the ammonia values present in the cyanide are effectively recovered for utilization in the overall process.

In accordance with the embodiment of FIG. 1, by hydrolyzing cyanide values prior to the recovery operation there is a reduced tendency to form polymers from the cyanide, ammonia and carbon dioxide which could cause solid deposition. In accordance with the embodiment of FIG. 2, there is obtained reduced energy and capital costs (the hydrolysis and $CO_2$ recovery are effected at similar conditions), at an increased solid deposition risk.

Numerous modifications and variations of the present invention are possible in light of the above teachings and, therefore, within the scope of the appended claims, the invention may be practiced otherwise than as particularly described.

What is claimed is:

1. In a process for producing nitriles wherein a nitrile production effluent includes gaseous ammonia, carbon dioxide and hydrogen cyanide, the improvement comprising:
   a. recovering from the nitrile production effluent hydrogen cyanide and at least a portion of the ammonia and carbon dioxide as an aqueous solution, said aqueous solution containing ammonium carbonate and ammonium cyanide;
   b. hydrolyzing cyanide present in said aqueous solution to ammonia and carbon monoxide;
   c. stripping carbon monoxide, carbon dioxide, water vapor and un-hydrolyzed hydrogen cyanide from the aqueous solution produced in step b to recover water free of cyanide and a stripped gas;
   d. separating the stripped gas into a gaseous stream of ammonia and carbon monoxide and an aqueous solution containing ammonium carbonate and ammonium cyanide;
   e. stripping carbon dioxide free of hydrogen cyanide from said aqueous solution from step d; and
   f. passing at least a portion of the aqueous solution from step e to step b.

2. The process of claim 1 wherein the hydrolyzing is effected at a temperature of from 100° F. to 400° F.

3. The process of claim 2 wherein stripped ammonia and carbon monoxide is recycled to the nitrile production.

4. The process of claim 3 wherein the stripping of step c is effected at a temperature of from 150° F. to 250° F. and at a pressure of from 1 to 2 atmosphere.

5. The process of claim 4 wherein the stripping of step e is effected at a temperature of from 200° F. to 400° F. and at a pressure of from 5 to 20 atmospheres.

6. The process of claim 5 wherein a portion of the aqueous solution from step e is recycled to step d.

7. The process of claim 6 wherein a portion of the water recovered in step c is passed to step e.

8. The process of claim 7 wherein step d is effected at a temperature of from 120° F. to 200° F. and a pressure of from 1 to 2 atmospheres.

9. In a process for producing nitriles wherein a nitrile production effluent includes gaseous ammonia, carbon dioxide and hydrogen cyanide, the improvement comprising:
   a. recovering from the nitrile production effluent hydrogen cyanide and at least a portion of the ammonia and carbon dioxide as an aqueous solution, said aqueous solution containing ammonium carbonate and ammonium cyanide;
   b. stripping from the aqueous solution of step a carbon dioxide, water vapor and hydrogen cyanide to recover water free of cyanide and a stripped gas;
   c. separating the stripped gas into a gaseous stream of ammonia and an aqueous solution containing ammonium carbonate and ammonium cyanide;
   d. hydrolyzing cyanide present in the aqueous solution from step c to ammonia and carbon monoxide;
   e. stripping carbon dioxide and carbon monoxide, free of cyanide, from the aqueous solution from step d; and
   f. passing at least a portion of the aqueous solution from step e to step b.

10. The process of claim 9 wherein the hydrolyzing is effected at a temperature of from 100° F. to 400° F.

11. The process of claim 10 wherein ammonia recovered in step c is recycled to the nitrile production.

12. The process of claim 11 wherein step b is effected at a temperature of from 150° F. to 250° F. and a pressure of from 1 to 2 atmospheres.

13. The process of claim 12 wherein step c is effected at a temperature of from 120° F. to 200° F. and a pressure of from 1 to 2 atmospheres.

14. The process of claim 13 wherein a portion of the aqueous solution from step e is passed to step c.

15. The process of claim 14 wherein step e is effected at a temperature of from 200° F. to 400° F. and at a pressure of from 5 to 20 atmospheres.

16. The process of claim 15 wherein a portion of the water recovered in step b is passed to step e.

* * * * *